United States Patent
Garrait et al.

(10) Patent No.: US 10,640,439 B2
(45) Date of Patent: May 5, 2020

(54) METHOD FOR PRODUCING 1-CHLORO-2,2-DIFLUOROETHANE

(71) Applicant: ARKEMA FRANCE, Colombes (FR)

(72) Inventors: Dominique Garrait, Charly (FR); Charlotte Herdt, Poissy (FR); Camille Scherpereel, Bourgoin Jallieu (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 16/333,600

(22) PCT Filed: Sep. 25, 2017

(86) PCT No.: PCT/FR2017/052559
§ 371 (c)(1),
(2) Date: Apr. 2, 2019

(87) PCT Pub. No.: WO2018/060576
PCT Pub. Date: Apr. 5, 2018

(65) Prior Publication Data
US 2020/0002253 A1    Jan. 2, 2020

(30) Foreign Application Priority Data
Sep. 27, 2016  (FR) ...................................... 16 59079

(51) Int. Cl.
| | | |
|---|---|---|
| *C07C 17/20* | (2006.01) | |
| *C07C 17/38* | (2006.01) | |
| *C07C 17/383* | (2006.01) | |
| *C07C 19/12* | (2006.01) | |

(52) U.S. Cl.
CPC ............ *C07C 17/206* (2013.01); *C07C 17/38* (2013.01); *C07C 17/383* (2013.01); *C07C 19/12* (2013.01)

(58) Field of Classification Search
None
See application file for complete search history.

(56) References Cited

FOREIGN PATENT DOCUMENTS

| | | |
|---|---|---|
| CN | 104692998 A | 6/2015 |
| WO | 2015/082812 A1 | 6/2015 |

OTHER PUBLICATIONS

WO2015/082812, English translation, Jun. 11, 2015, pp. 1-8 (Year: 2015).*
ISA/EP; International Search Report and Written Opinion for International Application No. PCT/FR2017/052559 dated Apr. 5, 2018, 11 pages.

* cited by examiner

*Primary Examiner* — Medhanit W Bahta
(74) *Attorney, Agent, or Firm* — NK Patent Law

(57) ABSTRACT

The invention relates to a method for producing 1-chloro-2,2-difluoroethane from 1,1,2-trichloroethane, comprising at least one step of separating 1-chloro-2,2-difluoroethane from the organic phase produced during the method; said step comprising a) purification of the organic phase obtained in step (iii) so as to form a first stream comprising 1-chloro-difluoroethane and hydrofluoric acid and a second stream comprising 1,1,2-trichloroethane; b) the elimination of the hydrofluoric acid from said first stream in order to form a third stream comprising 1-chloro-difluoroethane; and c) a purification of said third stream comprising 1-chloro-difluoroethane.

10 Claims, No Drawings

METHOD FOR PRODUCING 1-CHLORO-2,2-DIFLUOROETHANE

CROSS-REFERENCE TO RELATED APPLICATIONS

This application is a U.S. National Stage application of International Application No. PCT/FR2017/052559, filed on 25 Sep. 2017, which claims the benefit of French Patent Application No. 1659079, filed 27 Sep. 2016.

TECHNOLOGICAL FIELD OF THE INVENTION

The present invention relates to the field of saturated fluorinated hydrocarbons. It relates more particularly to a process for producing 1-chloro-2,2-difluoroethane from 1,1,2-trichloroethane.

TECHNOLOGICAL BACKGROUND OF THE INVENTION

1-Chloro-2,2-difluoroethane (HCFC-142) is not only known as a blowing agent in foam production, but also as a raw material in the production of pharmaceutical or agrochemical compounds.

A process for producing 1-chloro-2,2-difluoroethane from 1,1,2-trichloroethane and/or 1,2-dichloroethylene, comprising at least one step during which 1,1,2-trichloroethane and/or 1,2-dichloroethylene react or reacts with hydrofluoric acid in the gas phase so as to give a stream comprising 1-chloro-2,2-difluoroethane, hydrochloric acid, hydrofluoric acid and 1,1-dichloroethylene, is known from WO 2015/082812. The presence of 1,1-dichloroethylene can be an impediment in subsequent reaction steps.

The applicant has developed a process for producing 1-chloro-2,2-difluoroethane which does not have the drawbacks of the prior art, in particular a process which avoids the formation of 1,1-dichloroethylene.

SUMMARY OF THE INVENTION

The present invention relates to a process for producing 1-chloro-2,2-difluoroethane from 1,1,2-trichloroethane, comprising (i) at least one step during which the 1,1,2-trichloroethane reacts with hydrofluoric acid in the gas phase, optionally in the presence of an oxidizing agent, and in the presence or absence of a fluorination catalyst, so as to give a stream comprising 1-chloro-2,2-difluoroethane, hydrochloric acid, hydrofluoric acid and at least one compound A chosen from 1,2-dichloroethylenes (cis and trans), 1-chloro-2-fluoroethylenes (cis and trans), 1,2-dichloro-2-fluoroethane and unreacted 1,1,2-trichloroethane; (ii) at least one step of separating the compounds resulting from the reaction step, so as to give a first stream comprising hydrochloric acid and a second stream comprising hydrofluoric acid, 1-chloro-2,2-difluoroethane, at least one compound A and unreacted 1,1,2-trifluoroethane; (iii) at least one step of separating the second stream, so as to give an organic phase comprising the 1-chloro-2,2-difluoroethane, at least one compound A and unreacted 1,1,2-trichloroethane and a nonorganic phase comprising HF; (iv) at least one step of separating the 1-chloro-2,2-difluoroethane from the organic phase obtained in (iii); (v) optionally recycling, to step (i), the organic phase after separation in step (iv); and (vi) optionally recycling, to step (i), the nonorganic phase resulting from step (iii), characterized in that step (iv) comprises:

a) purification of the organic phase obtained in step (iii) so as to form a first stream comprising 1-chloro-2,2-difluoroethane, at least one compound A and hydrofluoric acid and a second stream comprising 1,1,2-trichloroethane;

b) elimination of the hydrofluoric acid from said first stream so as to form a third stream comprising 1-chloro-2,2-difluoroethane and at least one compound A;

c) purification, preferably distillation, of said third stream comprising 1-chloro-2,2-difluoroethane.

According to one preferred embodiment, step a) of purification of the organic phase obtained in (iii) is a distillation, preferably carried out at a temperature between 30 and 80° C. and at an absolute pressure of between 1 and 4 bar.

According to one preferred embodiment, the second stream comprising 1,1,2-trichloroethane is recycled to step (i), preferably after distillation thereof at a temperature of between 100 and 170° C. and at an absolute pressure of between 1 and 4 bar absolute.

According to one preferred embodiment, step b) comprises a step of washing said first stream so as to form an intermediate stream B comprising 1-chloro-2,2-difluoroethane and said at least one of the compounds A selected from the group consisting of cis-1,2-dichloroethylene, trans-1,2-dichloroethylene, cis-1-chloro-2-fluoroethylene, trans-1-chloro-2-fluoroethylene and 1,2-dichloro-1-fluoroethane and an intermediate stream C comprising hydrofluoric acid.

According to one preferred embodiment, said intermediate stream B is dried so as to form said third stream.

According to one preferred embodiment, the drying is carried out at a temperature of from 0 to 30° C. and an absolute pressure of between 1 and 4 bar. According to one preferred embodiment, the first stream obtained in step a) and the third stream obtained in step b) also comprise trans-1,2-dichloroethylene and optionally at least one of the compounds A selected from the group consisting of cis-1,2-dichloroethylene, cis-1-chloro-2-fluoroethylene, trans-1-chloro-2-fluoroethylene and 1,2-dichloro-1-fluoroethane.

According to one preferred embodiment, step c) comprises at least one distillation, preferably carried out preferentially by distillation at a temperature of between 35 and 79° C. and at an absolute pressure of between 1 and 4 bar.

According to one preferred embodiment, the first stream obtained in step a), the intermediate stream B and the third stream obtained in step b) comprise trans-1,2-dichloroethylene and at least one of the compounds A selected from the group consisting of cis-1,2-dichloroethylene, cis-1-chloro-2-fluoroethylene, trans-1-chloro-2-fluoroethylene and 1,2-dichloro-1-fluoroethane.

According to one preferred embodiment, the first stream obtained in step a), the intermediate stream B and the third stream obtained in step b) comprise 1-chloro-2,2-difluoroethane, trans-1,2-dichloroethylene and at least one of the compounds A selected from the group consisting of cis-1,2-dichloroethylene, cis-1-chloro-2-fluoroethylene, trans-1-chloro-2-fluoroethylene and 1,2-dichloro-1-fluoroethane.

According to one preferred embodiment, step c) forms a fourth stream comprising 1-chloro-2,2-difluoroethane and trans-1,2-dichloroethylene and a fifth stream comprising at least one of the compounds A selected from the group consisting of cis-1,2-dichloroethylene, cis-1-chloro-2-fluoroethylene, trans-1-chloro-2-fluoroethylene and 1,2-dichloro-1-fluoroethane.

DETAILED DESCRIPTION OF THE INVENTION

A subject of the present invention is thus a process for producing 1-chloro-2,2-difluoroethane from 1,1,2-trichloroethane. The process comprises the following steps:

(i) at least one step during which the 1,1,2-trichloroethane reacts with hydrofluoric acid in the gas phase, optionally in the presence of an oxidizing agent, and in the presence or absence of a fluorination catalyst, so as to give a stream comprising 1-chloro-2,2-difluoroethane, hydrochloric acid, hydrofluoric acid and at least one compound A chosen from 1,2-dichloroethylenes (cis and trans), 1-chloro-2-fluoroethylenes (cis and trans), 1,2-dichloro-2-fluoroethane and unreacted 1,1,2-trichloroethane;

(ii) at least one step of separating the compounds resulting from the reaction step, so as to give a first stream comprising hydrochloric acid and a second stream comprising hydrofluoric acid, 1-chloro-2,2-difluoroethane, at least one compound A and 1,1,2-trifluoroethane;

(iii) at least one step of separating the second stream, so as to give an organic phase comprising the 1-chloro-2,2-difluoroethane, at least one compound A and unreacted 1,1,2-trichloroethane and a nonorganic phase comprising HF;

(iv) at least one step of separating the 1-chloro-2,2-difluoroethane from the organic phase obtained in (iii);

(v) optionally recycling, to step (i), the organic phase after separation in step (iv); and (vi) optionally recycling, to step (i), the nonorganic phase resulting from step (iii).

According to one preferred embodiment, step (iv) comprises:

a) purification, preferably distillation, of the organic phase obtained in step (iii) so as to form a first stream comprising 1-chloro-2,2-difluoroethane, at least one compound A and hydrofluoric acid and a second stream comprising 1,1,2-trichloroethane;

b) elimination of the hydrofluoric acid from said first stream so as to form a third stream comprising 1-chloro-2,2-difluoroethane and at least one compound A;

c) purification, preferably distillation, of said third stream comprising 1-chloro-2,2-difluoroethane.

Use is preferably made of a catalyst in step (i) and advantageously in the presence of an oxidizing agent. The temperature of the reaction step is preferably between 150 and 400° C., advantageously between 200 and 350° C. The pressure at which the fluorination reaction is carried out is preferably between 1 and 30 bar absolute, advantageously between 3 and 20 bar absolute and more particularly between 3 and 15 bar.

The amount of hydrofluoric acid used in the reaction is preferably between 5 and 40 mol and advantageously between 10 and 30 mol per mole of HCC-140.

The contact time, defined as being the volume of catalyst/total volume flow rate of gas at the temperature and pressure of the reaction, may be between 2 and 200 seconds, preferably between 2 and 100 seconds, advantageously between 2 and 50 seconds.

The oxidizing agent, pure or mixed with nitrogen, may be chosen from oxygen and chlorine. Chlorine is preferably chosen.

The amount of oxidizing agent used is preferably between 0.01 mol % and 20 mol % per mole of F140, advantageously between 0.01 mol % and 0.2 mol % per mole of HCC-140.

An amount of oxidizing agent of between 1 mol % and 10 mol % relative to the F140 has given very promising results.

The catalyst used may be a bulk or supported catalyst. The catalyst may be based on a metal, in particular on a transition metal or an oxide, halide or oxyhalide derivative of such a metal. By way of example, mention may in particular be made of $FeCl_3$, chromium oxyfluoride, $NiCl_2$, $CrF_3$ and mixtures thereof.

By way of supported catalysts, mention may be made of those supported on carbon or based on magnesium, such as magnesium derivatives, in particular halides such as $MgF_2$ or magnesium oxyhalides, such as oxyfluorides, or based on aluminum such as alumina, activated alumina or aluminum derivatives, in particular halides, such as $AlF_3$ or aluminum oxyhalides, such as oxyfluoride.

The catalyst may also comprise cocatalysts chosen from Co, Zn, Mn, Mg, V, Mo, Te, Nb, Sb, Ta, P, Ni, Zr, Ti, Sn, Cu, Pd, Cd, Bi and rare earth metals, or mixtures thereof. When the catalyst is chromium-based, Ni, Mg and Zn are advantageously chosen as cocatalyst.

The cocatalyst/catalyst atomic ratio is preferably between 0.01 and 5.

Chromium-based catalysts are particularly preferred.

The catalyst used in the present invention may be prepared by co-precipitation of the corresponding salts, optionally in the presence of a support.

The catalyst may also be prepared by co-milling of the corresponding oxides.

Prior to the fluorination reaction, the catalyst is subjected to a step of activation with HF at a temperature preferably of between 100 and 450° C., advantageously of between 200 and 400° C. for a period of between 1 and 50 hours.

In addition to the HF treatment, the activation may be carried out in the presence of the oxidizing agent.

The activation steps may be carried out at atmospheric pressure or under a pressure up to 20 bar.

According to one preferred embodiment of the invention, the support may be produced from alumina with a high porosity. In a first step, the alumina is converted into aluminum fluoride, or into a mixture of aluminum fluoride and alumina, by fluorination using air and hydrofluoric acid, the degree of conversion of the alumina into aluminum fluoride depending essentially on the temperature at which the fluorination of the alumina is carried out (in general between 200° C. and 450° C., preferably between 250° C. and 400° C.). The support is then impregnated by means of aqueous solutions of chromium salts, nickel salts and optionally rare earth metal salts, or by means of aqueous solutions of chromic acid, of nickel salt or zinc salt, and optionally of salts or oxides of rare earths and of methanol (serving as chromium-reducing agent). As chromium, nickel or zinc salts and rare earth metal salts, use may be made of chlorides, or other salts, such as, for example, oxalates, formates, acetates, nitrates and sulfates or dichromate of nickel, and of rare earth metals, provided that these salts are soluble in the amount of water capable of being absorbed by the support.

The catalyst may also be produced by direct impregnation of the alumina (which in general is activated) by means of solutions of the chromium, nickel or zinc, and optionally rare earth metal, compounds mentioned above. In this case, the conversion of at least one portion (for example 70% or more) of the alumina into aluminum fluoride or aluminum oxyfluoride is carried out during the step of activating the metal of the catalyst.

The activated aluminas that can be used to produce the catalyst are well-known, commercially available products. They are generally produced by calcination of alumina hydrates (aluminum hydroxides) at a temperature of between 300° C. and 800° C. The (activated or non-activated) aluminas may contain large amounts of sodium (up to 1000 ppm) without this being detrimental to the catalytic performance levels.

The catalyst is preferably conditioned or activated, that is to say converted into constituents that are active and stable (under the reaction conditions), by means of a prior "activation" operation. This treatment can be carried out either "in situ" (in the fluorination reactor) or alternatively in a suitable device designed to withstand the activation conditions.

After impregnation of the support, the catalyst is dried at a temperature between 100° C. and 350° C., preferably 220° C. to 280° C. in the presence of air or nitrogen.

The dried catalyst is then activated in one or two steps with hydrofluoric acid, optionally in the presence of an oxidizing agent. The duration of this fluorination activation step may be between 6 and 100 hours and the temperature between 200 and 400° C.

Preferably, the separating step (ii) comprises at least one distillation, advantageously carried out at a temperature of between −60° and 120° C. and more particularly between −60 and 89° C. and an absolute pressure of between 3 and 20 bar, and advantageously between 3 and 11 bar.

In addition to the 1-chloro-2,2-difluoroethane, the hydrofluoric acid and the 1,1,2-trichloroethane, the organic phase obtained in step (iii) also comprises at least one of the compounds A selected from the group consisting of cis-1,2-dichloroethylene, trans-1,2-dichloroethylene, cis-1-chloro-2-fluoroethylene, 1,2-dichloro-1-fluoroethane and trans-1-chloro-2-fluoroethylene.

After the separation of the second stream in step (iii), the nonorganic phase obtained in (iii) preferably contains the majority of the HF initially present in the second stream compared with the organic phase also obtained in step (iii). The organic phase obtained in (iii) may contain hydrofluoric acid. The amount of hydrofluoric acid in the organic phase is less than the amount of hydrofluoric acid in the nonorganic phase. The molar ratio of the hydrofluoric acid present in the organic phase to the hydrofluoric acid present in the nonorganic phase is less than 1:10, preferably less than 1:50, in particular 1:100.

According to one embodiment, before the recycling to step (i), the nonorganic phase obtained in (iii) is purified so that the HF content is greater than or equal to 90% by weight. Preferably, this purification comprises at least one distillation, advantageously carried out at a temperature between −23 and 46° C. and an absolute pressure of between 0.3 and 3 bar.

Preferably, the separating step (iii) comprises at least one decanting step, advantageously carried out at a temperature of between −20 and 60° C. and more particularly between −20 and 10° C.

Preferably, the separating step (iv) comprises a step of purification of the organic phase obtained in (iii) making it possible to separate the 1-chloro-2,2-difluoroethane and the 1,1,2-trichloroethane. In addition to the 1-chloro-2,2-difluoroethane and the 1,1,2-trichloroethane, the organic phase obtained in step (iii) also comprises at least two, three, four or all of the compounds A selected from the group consisting of cis-1,2-dichloroethylene, trans-1,2-dichloroethylene, cis-1-chloro-2-fluoroethylene, 1,2-dichloro-1-fluoroethane and trans-1-chloro-2-fluoroethylene; and optionally hydrofluoric acid. Thus, the organic phase obtained in step (iii) may comprise trans-1,2-dichloroethylene or trans-1,2-dichloroethylene and cis-1-chloro-2-fluoroethylene or trans-1,2-dichloroethylene, cis-1-chloro-2-fluoroethylene and 1,2-dichloro-1-fluoroethane or trans-1,2-dichloroethylene, cis-1-chloro-2-fluoroethylene, 1,2-dichloro-1-fluoroethane and cis-1,2-dichloroethylene or trans-1,2-dichloroethylene, cis-1-chloro-2-fluoroethylene, 1-chloro-2-fluoroethylene, 1,2-dichloro-1-fluoroethane, cis-1,2-dichloroethylene and trans-1-chloro-2-fluoroethylene.

Preferably, step a) of purification of the organic phase obtained in (iii) is a distillation. In particular, the distillation of the organic phase obtained in (iii) is carried out at a temperature of from 10 to 100° C., preferably from 20 to 90° C., more preferentially from 30 to 80° C., and at an absolute pressure of from 0.3 to 8 bar, preferably from 0.5 to 6 bar, more preferentially from 1 to 4 bar.

According to one preferred embodiment, the first stream obtained in step a) and the third stream obtained in step b) comprise said at least one of the compounds A selected from the group consisting of cis-1,2-dichloroethylene, trans-1,2-dichloroethylene, cis-1-chloro-2-fluoroethylene, trans-1-chloro-2-fluoroethylene and 1,2-dichloro-1-fluoroethane. Preferably, the first stream obtained in step a) and the third stream obtained in step b) comprise at least two, three, four or all of the compounds A selected from the group consisting of cis-1,2-dichloroethylene, trans-1,2-dichloroethylene, cis-1-chloro-2-fluoroethylene, 1,2-dichloro-1-fluoroethane and trans-1-chloro-2-fluoroethylene.

Thus, the first stream obtained in step a) and the third stream obtained in step b) may comprise trans-1,2-dichloroethylene or trans-1,2-dichloroethylene and cis-1-chloro-2-fluoroethylene or trans-1,2-dichloroethylene, cis-1-chloro-2-fluoroethylene and 1,2-dichloro-1-fluoroethane or trans-1,2-dichloroethylene, cis-1-chloro-2-fluoroethylene, 1,2-dichloro-1-fluoroethane and cis-1,2-dichloroethylene or trans-1,2-dichloroethylene, cis-1-chloro-2-fluoroethylene, 1,2-dichloro-1-fluoroethane, cis-1,2-dichloroethylene and trans-1-chloro-2-fluoroethylene.

According to one preferred embodiment, the second stream comprising 1,1,2-trichloroethane is recycled to step (i), preferably after purification thereof, the purification in particular being a distillation at a temperature of from 20 to 300° C., preferably from 50 to 250° C., more preferentially from 75 to 200° C., in particular from 100 to 170° C. and at an absolute pressure of from 0.3 to 8 bar, preferably from 0.5 to 6 bar, more preferentially from 1 to 4 bar.

According to one preferred embodiment, the step makes it possible to eliminate the residual hydrofluoric acid present in the first stream. Thus, step b) comprises a step of washing said first stream so as to form an intermediate stream B comprising 1-chloro-2,2-difluoroethane and said at least one of the compounds A selected from the group consisting of cis-1,2-dichloroethylene, trans-1,2-dichloroethylene, cis-1-chloro-2-fluoroethylene, trans-1-chloro-2-fluoroethylene and 1,2-dichloro-1-fluoroethane and an intermediate stream C comprising hydrofluoric acid. The intermediate stream B may comprise 1-chloro-2,2-difluoroethane and at least two, three, four or all of the compounds A selected from the group consisting of cis-1,2-dichloroethylene, trans-1,2-dichloroethylene, cis-1-chloro-2-fluoroethylene, 1,2-dichloro-1-fluoroethane and trans-1-chloro-2-fluoroethylene. Preferably, the intermediate stream B may, in addition to the 1-chloro-2,2-difluoroethane, comprise trans-1,2-dichloroethylene or trans-1,2-dichloroethylene and cis-1-chloro-2-fluoroethylene or trans-1,2-dichloroethylene, cis-1-chloro-2-fluoroethylene and 1,2-dichloro-1-fluoroethane or trans-1,2-dichloroethylene, cis-1-chloro-2-fluoroethylene, 1,2-dichloro-1-fluoroethane and cis-1,2-dichloroethylene or trans-1,2-dichloroethylene, cis-1-chloro-2-fluoroethylene, 1,2-dichloro-1-fluoroethane, cis-1,2-dichloroethylene and trans-1-chloro-2-fluoroethylene.

Preferably, the washing step is carried out at a temperature of from 0 to 30° C. Preferably, the washing step is carried out at an absolute pressure of between 1 and 4 bar.

Preferably, said intermediate stream B is dried so as to form said third stream. In particular, the drying is carried out at a temperature of from 0 to 30° C. Preferably, the drying is carried out at an absolute pressure of between 1 and 4 bar.

According to one particular embodiment, the first stream obtained in step a), the intermediate stream B and the third stream obtained in step b) comprise 1-chloro-2,2-difluoroethane, trans-1,2-dichloroethylene and at least one of the compounds A selected from the group consisting of cis-1,2-dichloroethylene, cis-1-chloro-2-fluoroethylene, trans-1-chloro-2-fluoroethylene and 1,2-dichloro-1-fluoroethane. Preferably, the first stream obtained in step a), the intermediate stream B and the third stream obtained in step b) comprise 1-chloro-2,2-difluoroethane, trans-1,2-dichloroethylene and at least one, two, three or all of the compounds A selected from the group consisting of cis-1,2-dichloroethylene, cis-1-chloro-2-fluoroethylene, 1,2-dichloro-1-fluoroethane and trans-1-chloro-2-fluoroethylene.

Preferably, the intermediate stream C comprising hydrofluoric acid may be recycled into step (i).

According to one preferred embodiment, the third stream obtained in step b) is purified in step c). Said purification is preferably a distillation. Thus, step c) may be a distillation carried out at a temperature between 35 and 79° C., preferably at an absolute pressure of between 1 and 4 bar.

As mentioned above, the third stream obtained in step b) comprises 1-chloro-2,2-difluoroethane, trans-1,2-dichloroethylene and at least one of the compounds A selected from the group consisting of cis-1,2-dichloroethylene, cis-1-chloro-2-fluoroethylene, trans-1-chloro-2-fluoroethylene and 1,2-dichloro-1-fluoroethane. Thus, step c) of the present process makes it possible to form a fourth stream comprising 1-chloro-2,2-difluoroethane and trans-1,2-dichloroethylene and a fifth stream comprising at least one of the compounds A selected from the group consisting of cis-1,2-dichloroethylene, cis-1-chloro-2-fluoroethylene, trans-1-chloro-2-fluoroethylene and 1,2-dichloro-1-fluoroethane.

According to one preferred embodiment, the fifth stream may comprise at least one, two, three or all of the compounds A selected from the group consisting of cis-1,2-dichloroethylene, cis-1-chloro-2-fluoroethylene, 1,2-dichloro-1-fluoroethane and trans-1-chloro-2-fluoroethylene, if the third stream comprises at least one, two, three or all of the compounds A selected from the group consisting of cis-1,2-dichloroethylene, cis-1-chloro-2-fluoroethylene, 1,2-dichloro-1-fluoroethane and trans-1-chloro-2-fluoroethylene, as mentioned above.

According to one particular embodiment, said first stream obtained in step a), the intermediate stream B, the third stream obtained in step b) and/or the fourth stream are devoid of 1,1-dichloroethylene. The absence of 1,1-dichloroethylene in said first stream obtained in step a) and/or said intermediate stream B and/or said third stream obtained in step b) and/or the fourth stream is thus obtained by virtue of the present invention.

The invention claimed is:

1. A process for producing 1-chloro-2,2-difluoroethane from 1,1,2-trichloroethane, comprising:
    (i) at least one step comprising reacting the 1,1,2-trichloroethane with hydrofluoric acid in the gas phase, in the presence or absence of a fluorination catalyst, so as to give a stream comprising 1-chloro-2,2-difluoroethane, hydrochloric acid, hydrofluoric acid, unreacted 1,1,2-trichloroethane and at least one compound A selected from the group consisting of 1,2-dichloroethylenes (cis and trans), 1-chloro-2-fluoroethylenes (cis and trans), and 1,2-dichloro-2-fluoroethane;
    (ii) at least one step comprising separating the compounds resulting from the reaction step, so as to give a first stream comprising hydrochloric acid and a second stream comprising hydrofluoric acid, 1-chloro-2,2-difluoroethane, at least a portion of the at least one compound A and unreacted 1,1,2-trichloroethane;
    (iii) at least one step comprising separating the second stream, so as to give an organic phase comprising the 1-chloro-2,2-difluoroethane, at least a portion of the at least one compound A, HF and unreacted 1,1,2-trichloroethane and a nonorganic phase comprising HF; and
    (iv) at least one step comprising separating the 1-chloro-2,2-difluoroethane from the organic phase obtained in (iii); wherein step (iv) comprises:
        a) purifying the organic phase obtained in step (iii) so as to form a first stream comprising 1-chloro-2,2-difluoroethane, at least a portion of the at least one compound A and hydrofluoric acid and a second stream comprising 1,1,2-trichloroethane;
        b) eliminating the hydrofluoric acid from said first stream so as to form a third stream comprising 1-chloro-2,2-difluoroethane and at least a portion of the at least one compound A; and
        c) purifying said third stream comprising 1-chloro-2,2-difluoroethane.

2. The process as claimed in claim 1, wherein step a) of purification of the organic phase obtained in (iii) is a distillation, carried out at a temperature between 30 and 80° C. and at an absolute pressure of between 1 and 4 bar.

3. The process as claimed in claim 1, wherein the second stream comprising 1,1,2-trichloroethane from step (iv)(a) is recycled to step (i).

4. The process as claimed in claim 1, wherein step b) comprises a step of washing said first stream so as to form an intermediate stream B comprising 1-chloro-2,2-difluoroethane and said at least one of the compounds A selected from the group consisting of cis-1,2-dichloroethylene, trans-1,2-dichloroethylene, cis-1-chloro-2-fluoroethylene, trans-1-chloro-2-fluoroethylene and 1,2-dichloro-2-fluoroethane and an intermediate stream C comprising hydrofluoric acid.

5. The process as claimed in claim 4, wherein said intermediate stream B is dried so as to form said third stream.

6. The process as claimed in claim 5, wherein the drying is carried out at a temperature of from 0 to 30° C. and an absolute pressure of between 1 and 4 bar.

7. The process as claimed in claim 1, wherein the first stream obtained in step a) and the third stream obtained in step b) also comprise trans-1,2-dichloroethylene.

8. The process as claimed in claim 1, wherein step c) comprises at least one distillation.

9. The process as claimed in claim 4, wherein the first stream obtained in step a), the intermediate stream B and/or the third stream obtained in step b) comprise trans-1,2-dichloroethylene and at least one of the compounds A selected from the group consisting of cis-1,2-dichloroethylene, cis-1-chloro-2-fluoroethylene, trans-1-chloro-2-fluoroethylene and 1,2-dichloro-2-fluoroethane.

10. The process as claimed in claim 1, wherein the at least one compound A comprises trans-1,2-dichloroethylene and step c) forms a fourth stream comprising 1-chloro-2,2-difluoroethane and trans-1,2-dichloroethylene and a fifth stream comprising at least one of the compounds A selected from the group consisting of cis-1,2-dichloroethylene, cis-1-chloro-2-fluoroethylene, trans-1-chloro-2-fluoroethylene and 1,2-dichloro-1-fluoroethane.

* * * * *